United States Patent [19]

Hatch et al.

[11] Patent Number: 4,565,632
[45] Date of Patent: Jan. 21, 1986

[54] CHROMATOGRAPHIC CARTRIDGE COLUMN SYSTEM

[75] Inventors: Richard G. Hatch, Berkeley; Gary Tepermeister, Pleasant Hill, both of Calif.

[73] Assignee: Beckman Instruments, Inc., Fullerton, Calif.

[21] Appl. No.: 690,565

[22] Filed: Jan. 11, 1985

[51] Int. Cl.[4] ............................................. B01D 15/08
[52] U.S. Cl. .................................... 210/656; 55/386; 210/198.2
[58] Field of Search ................. 210/656, 198.2; 55/67, 55/197, 386

[56] References Cited

U.S. PATENT DOCUMENTS 3,440,864  4/1969  Blume .............................. 210/198.2
4,451,364  5/1984  Higgins ............................ 210/198.2
4,522,715  6/1985  Walters ........................... 210/198.2

Primary Examiner—John Adee
Attorney, Agent, or Firm—W. H. May; P. R. Harder; L. D. Rish

[57] ABSTRACT

End caps that are press fitted to the ends of an analytical column tube and to a precolumn tube are abutted to form a fluid flow path. The end caps include projections around the fluid flow path to form a void between the opposing faces of the end caps. A gasket seal is retained within the void to provide a seal for confining pressurized fluid to the flow path. The analytical column extends into a stepped bore in a holder body. A wider diameter portion of the stepped bore receives the analytical column end cap and provides a stop for supporting the compressive load required to maintain the seal.

12 Claims, 7 Drawing Figures

CHROMATOGRAPHIC CARTRIDGE COLUMN SYSTEM

BACKGROUND OF THE INVENTION

This invention relates generally to couplers for tubes carrying highly pressurized fluids and particularly to high pressure liquid chromatography column and tube couplers. Still more particularly, this invention relates to cartridge columns for high pressure liquid chromatography.

Liquid chromatography is used for chemical analysis and for chemical product isolation or purification. A porous material is held stationary within a chamber, such as a relatively long column, and a mobile liquid material is forced through the porous material. Typically the porous material is an inert powder with a chemically modified surface. The mobile liquid comprises a carrier liquid and other dissolved chemical substances into which a sample is injected for separation into its components. The components of the sample have varying affinities for the stationary porous material. Therefore, as the mobile liquid moves through a chromatographic column, the chemical substances experience delays that are functions of their affinities for the stationary porous material.

The column separates the chemical substances into layers or zones that emerge from the column at different times. The emergence of each substance from the column is detected by a refractometer, an ultra-violet light, an absorbtometer or other suitable analytical apparatus through which the mobile liquid flows after leaving the column.

The useful life of a column may be greatly shortened by particles or chemical contaminants in the mobile liquid or in the sample input to the column. These contaminants can be trapped in a small, inexpensive precolumn connected in series upstream from the analytical column. When performance of the chromatographic system has deteriorated, the precolumn may be replaced to restore performance of the system. Previously available precolumn devices are either mechanically complex and therefore, difficult and expensive to manufacture or have deficiencies such as constrictions in the flow path that cause disturbances in the flow profile of the liquid stream.

Although it is possible to interconnect the analytical column and the precolumn with a length of capillary tubing and associated connectors, that method is expensive and introduces substantial extra mixing volume and other extra column effects. The analytical column and the precolumn are typically held within a holder body under compression by a pair of end caps. Normally capillary tubing is connected to the end caps and sealed thereto against conical seats in the ends of the end caps. The seats are subject to wear as the capillary tubing is connected and disconected so that the end caps must be periodically replaced.

Previous high pressure liquid chromatography tubing connectors introduce radical changes in the diameter of the flow path thereby forming spaces in which fluids from one part of the stream of mobile fluid can collect and then intermix with fluids from another part of the stream. Non-uniformity in the fluid flow between the precolumn and the analytical column is undesirable because it causes eddies and stationary regions within the mobile fluid, which impair the ability of the column to separate the mobile liquid into layers. An efficient analytical column will produce narrow, symmetric bands and will cause the detecting instrument to produce a sharp peak for each substance in the mobile liquid. Previous high pressure liquid chromatography systems cause distortion in the peak shape because the edges of the layers are asymmetrical. The detector produces an output signal peak each time a substance enters the detector, indicating incomplete separation of the chemical substances when the flow path includes eddies and dead spaces.

SUMMARY OF THE INVENTION

The present invention provides a chromatographic cartridge column system that overcomes the disadvantages of previous systems. The chromatographic cartridge column system of the present invention avoids the use of threading the ends of either the analytical column or the precolumn and further avoids the use of fluid loaded seals. The chromatographic cartridge column system of the present invention employs a simple, inexpensive gasket seal and a direct butt connection between the precolumn and the analytical column with no constriction in the flow path diameter for high pressure operation.

A holder body has a stepped bore therein for retaining the analytical column and the precolumn. A step betwen a narrower bore portion and a wider bore portion acts as a stop which engages an end cap mounted to the analytical column. An end nut that is engaged with an end of the holder body urges the precolumn toward the analytical column end cap, which is then urged against the step. A force of several hundred pounds may be required to effect adequate sealing between the analytical column and the precolumn. Application of the sealing force to the end cap of the analytical column, rather than to the entire column prevents the analytical column from buckling.

A first filter is retained in a cavity between the end cap and the end of the analytical column tube. A second filter is retained in a cavity between the precolumn tube and an end cap attached thereto. Each of the filters includes a border that engages the ends of the tubes and end cap passages to retain the filters in the proper position.

Each of the end caps includes a central projection around the flow path of the high pessure liquid. The end cap on the analytical column has an outwardly projecting ring portion that forms a cavity having a diameter slightly larger than that of the diameter of the precolumn end cap. The precolumn end cap is inserted into the cavity so that the portions are positioned end-to-end and the filters and flow paths in the precolumn and the analytical column are aligned. A gasket seal that is formed of a suitable elastomeric material is retained between the end caps around the projections. The end caps preferably include bosses that face the gasket seal and compress it axially when the end nut is secured to the holder body. The bosses act as seal retainers to prevent the seal from flowing under the force of the pressurized fluid flowing from the precolumn to the analytical column.

DESCRIPTION OF THE PREFERRED EMBODIMENT

Figure 1:
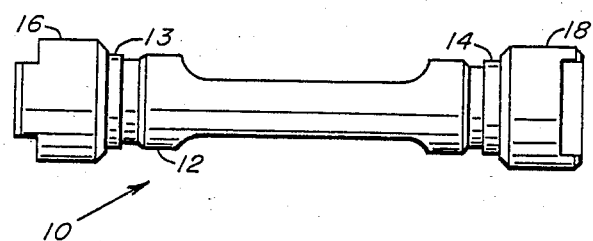
FIG. 1 is a plan view of a chromatographic cartridge column system according to the invention.

Referring to FIG. 1, a chromatographic cartridge column system 10 according to the invention includes a holder body 12 having a pair of threaded ends 13, 14 upon which a pair of end nuts 16, 18, respectively, are engaged. The holder body 12 and the end nuts 16, 18 are preferably made of a suitable metal such as brass, stainless steel, or aluminum.

Figure 2:
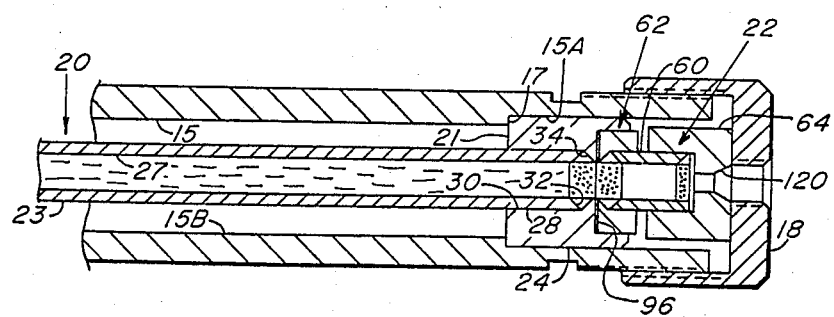
FIG. 2 is a cross sectional view of the system of FIG. 1 showing a chromatographic analytical column, a precolumn and seals at the ends of the analytical column and the precolumn.

As shown in FIG. 2, the holder body 12 includes a central passage 15 having a stepped diameter. A step 17 divides the central passage 15 into a first portion 15A and a second portion 15B with the second portion 15B having the smaller diameter.

Referring to FIG. 2, the end nut 18 retains an analytical column 20 and a precolumn 22 within the central passage 15 in the holder body 12. The analytical column 20 comprises a tube 23 having a central passage 27 and an end 28. An end cap 24 is mounted to the end 28. The end cap 24 includes an end portion 21 that is retained against the step 17 when the end nut 18 is secured upon the holder body 12.

Figure 3:
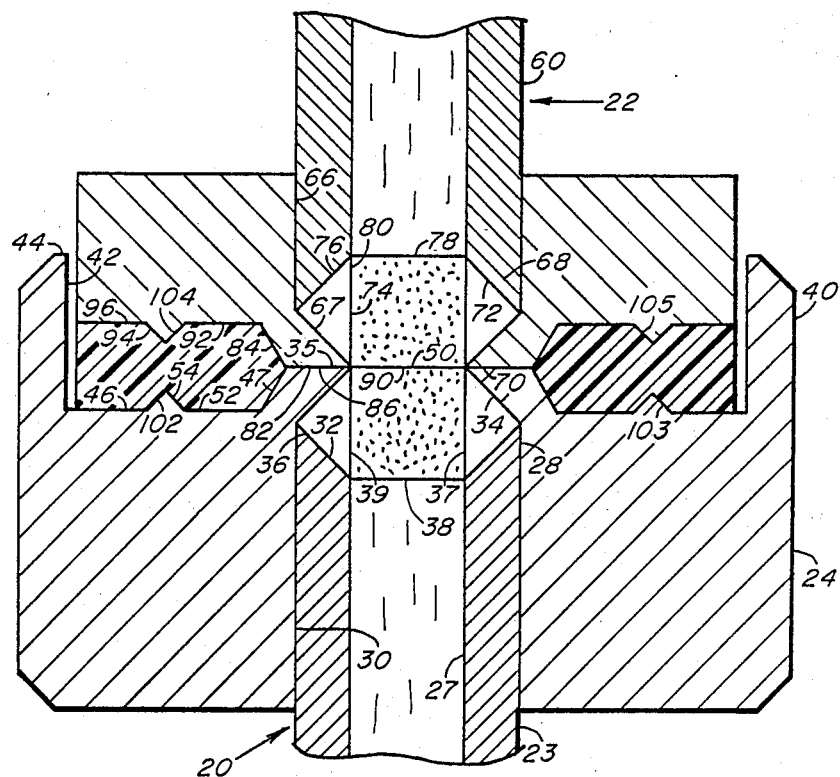
FIG. 3 is an enalrged view of a sealing arrangement included in the apparatus of FIGS. 1–2.

Referring to FIGS. 2 and 3, the end cap 24 includes a first hollow cylindrical bore 30 that is press fitted upon the end 28 of the tube 23. The outermost portion of the end 28 defines a frustoconical portion 32 that tapers into the interior of the tube 23 such that the narrower end of the frustonical portion 32 has substantially the same diameter as the central passage 27 and the wider end of the frustoconical portion 32 is substantially the same diameter as the tube 23. The end cap 24 defines a frustoconical portion 34 that has its narrower end at an end surface 35 of the end cap 24. The frustoconical portion 34 widens away from the surface 35 such that the wider end of the frustoconical portion 34 is inside the passage 30. When the end cap 24 is press fitted upon the analytical column 20, the wider ends of the frustoconical portions 32 and 34 are adjacent. The end 28 abuts the wider portion of the frustoconical portion 34, which acts as a stop to limit penetration of the tube 23 into the cavity 30.

The frustoconical portion 32 may be formed by machining the end 28 of the tube 23, and the frustoconical portion 34 may be formed by machining the bore 30 to be suitably tapered at the end that abuts the end 28 of the analytical column 20.

When the chromatographic cartridge column system 10 is fully assembled, the two frustoconical portions 32 and 34 cooperate to enclose a volume 37 that is essentially a ring having a triangular cross section, as best shown in FIG. 3. A filter border 36 is retained within the region 37 bounded by the frustoconical end 32 of the analytical column and the frustoconical portion 34 of the end cap 24. A filter 38 is retained within a cylindrical region 39 inside the filter border 36.

Figure 6:
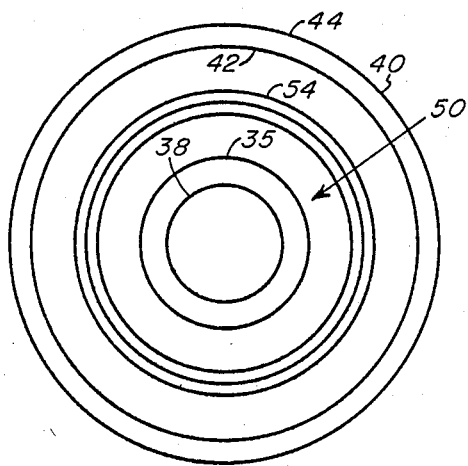
FIG. 6 is an enlarged end view of the analytical column and an end cap that abuts the end of the precolumn shown in FIG. 6.
Figure 7:
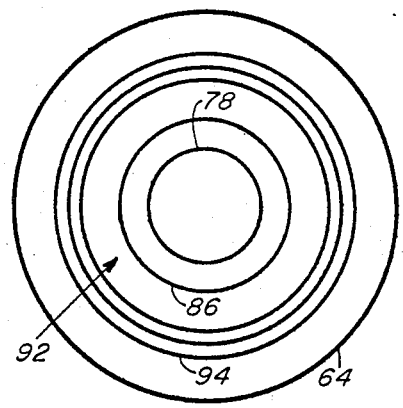
FIG. 7 is an enlarged end view of the precolumn shown in FIGS. 2–5.

Referring to FIGS. 2, 3 and 6, the end cap 24 includes a ring portion 40 that extends beyond the end 28. The ring portion 40 encloses a generally cylindrical cavity 42 having an outer end 44 and an inner end 46. The inner end 46 includes a central projection 47 formed as a frustocone that terminates in the surface 35, which surrounds and end 50 of the filter 38. The surface 35 is preferably generally planar. The inner end 46 includes a second surface 52 around the projection 47. The surface 52 may be formed by machining the inner end 46 around the surface 35 to form the projection 47. The surface 52 is generally planar except for a small outwardly projecting annular boss 54 that is located approximately half of the radial distance from the outer edge of the projection 47 to the inner edge of the ring portion 40. The boss 54 is shown to have a generally triangular cross section, but other configurations, such as a portion of a circle may be satisfactorily used.

Referring to FIGS. 2 and 3, the precolumn 22 includes a tube 60 and a pair of end caps 62, 64. The inside and outside diameters of the tubes 23 and 60 are substantially identical. However, the end cap 62 has an outside diameter that is slightly less than that of the cavity 42 so that when the chromatographic cartridge column system 10 is fully assembled, the end cap 62 fits within the cavity 42.

The end cap 62 includes a generally cylindrical cavity 66 into which an end 68 of the tube 60 is press fitted. The cavity 66 terminates in a frustoconical portion 67 that has its wider end inside the end cap 62 and its narrower end adjacent a surface 70 of the end cap 62. The end 68 of the tube 60 defines a frustoconical volume 72 that is similar to the frustoconical volume 32 in the end 28 of the tube 23. The frustoconical volume 72 is configured such that the narrower end is inside the tube 62. When the chromatographic cartridge column system 10 is assembled, the wider end of the frustoconical volume 72 is adjacent the wider is end of the frustoconical portion 67 of the end cap 62. The juncture of the end cap 62 and the wider end of the frustoconical volume 72 functions as a stop to limit penetration of the tube 60 into the end cap 62. When the end cap 62 and the tube 60 are properly connected together as best shown in FIG. 3, the frustoconical portions 67 and 72 cooperate to enclose a volume 74 that is formed as a ring having a triangular cross section.

A filter border 76 that is preferably substantially identical to the filter border 36 is placed inside the cavity 66 before insertion of the tube 60. The filter border 76 is therefore retained within the volume 74 bounded by the frustoconical portions 67 and 72. A filter 78, which is substantially identical to the filter 38 is placed in a cylindrical cavity 80 in the filter border 76.

The end cap 62 includes an end 82 that faces toward the inner end 46 of the cavity 42 when the chromatographic cartridge column system 10 is assembled. The end 82 includes a central projection 84 that terminates in a generally planar surface 86, which includes the narrower end of the frustoconical portion 72 and which is preferably coplanar with an edge 90 of the filter 78.

The end 82 includes a second surface 92 around the projection 84. The surface 92 may be formed by machining the inner end 82 around the surface 86 to form the projection 84. The surface 92 is generally planar except for a small outwardly projecting annular bass 94 that is located opposite the boss 54 when the chromatographic cartridge column system 10 is assembled. The boss 94 preferably has a cross section that is substantially identical to that of the boss 54.

Figure 4:
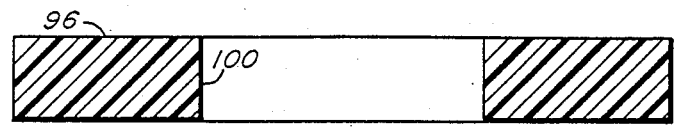
FIG. 4 is an enlarged cross sectional view of a seal shown in FIGS. 2–3 between the column and the precolumn before assembly of the chromatographic cartridge column system of the invention.

A seal 96 is placed between the surfaces 52 and 92 of the end caps 24 and 62, respectively. Referring to FIG. 4, the seal 96 is formed as a flat washer having a central orifice 100 therethrough. The central orifice 100 has approximately the same diameter as the projections 47 and 84. When the end nut 18 is suitably engaged upon the holder body 12, the seal 96 is compressed between the surfaces 52 and 92 to prevent leakage of pressurized fluid passing from the precolumn 22 into the analytical column 20. The bosses 54 and 94 cooperate to form a plurality of indentations 102-105 in the seal 96. The bosses 54 and 94 and the corresponding indentations 102-105 cooperate to lock the seal 96 between the surfaces 52, 92 of the end caps 24, 62, respectively, and prevent the seal 96 from moving out of sealing engagement with the surfaces 52, 92 when pressurized fluid passes through the passages 66 and 27.

The dimensions of the projections 47, 86 and the bosses 54, 94 may vary depending upon the pressures to be contained within the precolumn 22 and the analytical column 20. It has been found that having the projection 47 and the boss 54 extends about 0.01 inch and 0.006 inch, respectively, above the plane of the surface 52 is satisfactory for high pressure liquid chromatography applications at pressures of about 8000 psi in standard 4.6 mm inside diameter chromatography tubing. The projection 86 and the boss 94 preferably have dimensions that are substantially identical to those of the projection 47 and the boss 54. The seal 96 in cooperation with the surfaces 52, 92 and the bosses 54, 94 has been found to be effective in containing fluids within the analytical column 20 and the precolumn 22 pressurized to about 10,000 psi.

In order to be effective for containing the pressurized fluid in the precolumn 22 and the analytical column 20, the seal 96 must be held under compression by a force at least as great as the force developd by the liquid pressure acting on the area the seal 96 encircles. At high pressures, such as 8000 to 10,000 psi, used in high pressure liquid chromatography the force may be several hundred pounds, depending upon the area exposed to the fluid pressure. Application of the compressive force required to the provide adequate sealing to the entire length of the analytical column 20 creates a risk of buckling when the analytical column 20 is formed of standard tubing commonly used in liquid chromatography. The chromatographic cartridge column system 10 according to the invention prevents buckling of the analytical column 20 by having the sealing force applied to the end cap 24, rather than to the tube 23. The precolumn 22 is preferably relatively short in length compared to its diameter so that there is no danger of damage to the precolumn 22 in applying the sealing force along its entire length. Retaining the seal 96 between the surfaces 52 and 92 with the bosses 54 and 94 permits exposure of a relatively large area to the liquid pressure, the end caps 24 and 62 may be butted together to provide a flow path having a uniform diameter from the precolumn 22 to the analytical column 20.

Figure 5:
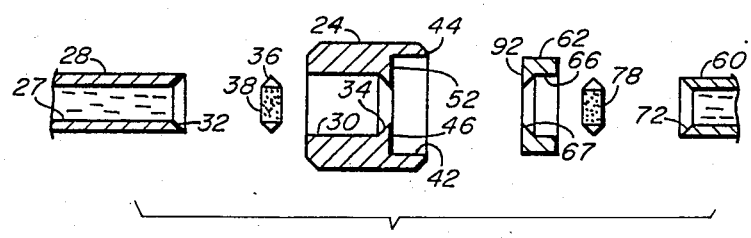
FIG. 5 is an exploded view of the apparatus shown in FIG. 2.

Referring to FIG. 5, the analytical column 20 is assembled by forming the bore 30 in the end cap 24 and tapering the end of the bore 30 to form the frustoconical portion 34. The cavity 42 in the end cap 24 is formed to receive the end cap 62 of the precolumn 22. The filter 38 and filter border 36 are inserted into the cavity 30 and positioned such that the filter border 30 seats against tapered end of the passage 30. The frustoconical portion 32 is formed in the end 28 of the tube 23, which is inserted into the passage 30. The outer diameter of the tube 23 is slightly larger than the inner diameter of the passage 30 so that the end cap is press fitted upon the tube 23 when the tube 23 is inserted into the passage 30.

The passage 66 in the end cap 62 is formed to have a slightly smaller diameter than the outside diameter of the tube 60, and the frustoconical portion 67 is formed at the end of the passage 66 to receive the filter border 76. The frustoconical portion 72 is formed in the end of the tube 60, and the filter 78 is inserted into the passage 66 followed by the tube 60.

The analytical column is then inserted into the holder body 12 such that the end cap 24 engages the step 17 in the passage 15. The filter 96 and the end cap 62 are inserted into the cavity 42 in the end cap 24. The end nut 16 is secured to the holder body with sufficient force to provide the desired sealing between the abutted end caps 24 and 62.

The end cap 64 preferably includes a frustoconical seat 120 respectively, in their outer ends for forming seals with a capillary tubing connector(not shown) that is ordinarily used to connect the column cartridge system 10 to other apparatus (not shown). Therefore, when the seat 120 becomes worn, it is not necessary to replace the end cap 18, as is required in the prior art.

The end caps 24, 62, the end nuts 16, 18 and the tubes 23, 60 are preferably formed of 316 stainless steel. The seal 96 is preferably formed of polytetrafluoroethylene (PTFE), but other suitable polymeric materials, such as polyimides, or a soft metal, such as silver, may be used to form the seal 76. Chemical and thermal stability requirements ordinarily will determine the material for forming the seal 96. The filters 38 and 78 are preferably formed of fritted disks of Hastelloy C or type 316 stainless steel, and the borders 36 and 76 are preferably formed of a fluoropolymeric material such as CTFE, which 3M Company sells under the trademark "KEL-F".

What is claimed is:

1. A liquid chromatography cartridge column assembly including an analytical column having an analytical column bore and a precolumn having a precolumn bore, comprising:

a holder body having a bore therein;

a first end cap mounted upon an end of the analytical column, the first end cap having a first end configured to fit slidably within the bore;

stop means for limiting movement of the first end cap within the bore;

a second end cap mounted upon an end of the precolumn, the second end cap having a portion configured to abut the first end cap to form a fluid flow path between the analytical column bore and the precolumn bore; and means cooperating with said stop means for forming a seal between the first and second end caps and around the fluid flow path.

2. The liquid chromatography cartridge column assembly of claim 1 wherein the stop means comprises a first bore portion having a first diameter for receiving the first end cap therein, a second bore portion axially aligned with the first bore portion for receivng the analytical column therein, the second bore portion having a second diameter less than the first diameter, the first and second bore portions intersecting to form a step, the step being positioned to bear against the first end of the first end cap to limit movement of the first end cap into the bore.

3. The liquid chromatography cartridge column assembly of claim 1 wherein the seal means comprises:
   a first projection extending from a second end of the first end cap around the fluid flow path;
   a second projection extending from the second end cap around the fluid flow path in abutment with the first projection such that the first projection and the second projection cooperate to form a void around the fluid flow path;
   a gasket seal positioned within the void; and
   means for retaining the gasket seal within the void.

4. The liquid chromatography cartridge column assembly of claim 3 wherein the retaining means includes:
   a first annular boss around the first projection; and
   means for compressing the gasket seal against the first annular boss.

5. The liquid chromatography cartridge column assembly of claim 4 wherein the retaining means includes a second annular boss around the second projection, the first and second annular bosses being in opposing relationship when the analytical column and the precolumn are aligned to form the fluid flow path such that the gasket seal is compresssed between the first and second annular bosses.

6. The liquid chromatography cartridge column assembly of claim 3 wherein the retaining means includes:
   an annular boss around the second projection; and
   means for compressing the gasket seal against the annular boss.

7. A liquid chromatography cartridge column assembly including an analytical column having an analytical column bore and a precolumn having a precolumn bore, comprising:
   a holder body having a stepped bore therein, the stepped bore including a first bore portion having a first diameter and a second bore portion having a second diameter, the first diameter being greater than the second diameter, the first and second bore portions being axially aligned and intersecting at a step;
   a first end cap mounted upon an end of the analytical column, the first end cap having a first end configured to fit slidably within the first bore portion to be retained against the step, the first end cap having a second end having a cavity therein;
   a second end cap mounted upon the precolumn, the second end cap having a portion configured to fit slidably within the cavity when the first end cap and the second end cap are abutted with the analytical column bore and the precolumn bore in axial alignment to form a fluid flow path; and
   means for forming a seal between the first and second end caps and around the fluid flow path.

8. A method for forming a high pressure seal around a fluid flow path formed by abutting a first end cap mounted to a chromatographic analytical column and a second end cap mounted to a precolumn, comprising the steps of:
   forming a stepped bore in a holder body;
   forming a first end of the first end to fit slidably within the bore;
   limiting movement of the first end cap within the bore by a stop within the stepped bore;
   placing the second end cap in abutment with the first end cap to place the analytical column bore and the precolumn bore in axial alignment to form a fluid flow path;
   placing a seal between the first and second end caps and around the fluid flow path; and
   compressing the precolumn and the first endcap between an end nut and the stop to compress the seal between the first and second end caps to confine pressurized liquids in the analytical column and the precolumn to the fluid flow path therebetween.

9. The method of claim 8, further including the steps of:
   forming a first projection extending from a second end of the first end cap around the fluid flow path;
   forming a second projection extending from the second end cap around the fluid flow path in abutment with the first projection such that the first projection and the second projection cooperate to form a void around the fluid flow path;
   placing a gasket seal within the void; and
   retaining the gasket seal under compression within the void.

10. The method of claim 9, further including the steps of:
    forming a first annular boss around the first projection; and
    compressing the gasket seal against the first annular boss.

11. The method of claim 10, further including the steps of:
    forming second annular boss around the second projection such that the first and second annular bosses are in opposing relationship when the analytical column and the precolumn are aligned to form the fluid flow path; and
    compressing the gasket seal between the first and second annular bosses.

12. The method of claim 7, further including the steps of:
    forming an annular boss around the second projection; and
    compressing the gasket seal against the annular boss.

* * * * *